United States Patent [19]
Pearson et al.

[11] Patent Number: 5,541,413
[45] Date of Patent: Jul. 30, 1996

[54] ACOUSTO-OPTIC TUNABLE FILTER-BASED SURFACE SCANNING SYSTEM AND PROCESS

[75] Inventors: Lee H. Pearson, Bear River; Kendall B. Johnson, Logan; Timothy E. Doyle, Roy, all of Utah

[73] Assignee: Thiokol Corporation, Ogden, Utah

[21] Appl. No.: 307,734

[22] PCT Filed: Apr. 23, 1993

[86] PCT No.: PCT/US93/03831

§ 371 Date: Sep. 26, 1994

§ 102(e) Date: Sep. 26, 1994

[87] PCT Pub. No.: WO93/22655

PCT Pub. Date: Nov. 11, 1993

Related U.S. Application Data

[63] Continuation-in-part of Ser. No. 873,937, Apr. 24, 1992, abandoned.

[51] Int. Cl.$^6$ .......................... G01N 21/17; G01N 21/35; G01N 21/64
[52] U.S. Cl. ................. 250/339.11; 250/301; 250/341.8; 250/461.1; 356/445; 356/446
[58] Field of Search ................................... 356/445, 446; 250/301, 339.11, 341.8, 461.1

[56] References Cited

U.S. PATENT DOCUMENTS

| | | | |
|---|---|---|---|
| 2,404,064 | 7/1946 | Heigl et al. | 250/339.12 |
| 2,516,672 | 7/1950 | Brockman | 338/18 |
| 2,562,525 | 7/1951 | Cary | 250/339.07 |
| 2,634,908 | 4/1953 | Jackson, Jr. et al. | 364/856 |

(List continued on next page.)

FOREIGN PATENT DOCUMENTS 3-115838  5/1991  Japan.

OTHER PUBLICATIONS

E. Neil Lewis et al., "A Miniaturized, No-Moving-Parts Raman Spectrometer," *Applied Spectroscopy*, vol. 47, No. 5, pp. 539–543 (1993).

Chieu D. Tran and Ricardo J. Furlan, "Acousto-Optic Tunable Filter as a Polychromator and Its Application in Multidimensional Fluorescence Spectrometry," *Anal. Chem.*, vol. 64, No. 22, pp. 2775–2782 (Nov. 15, 1992).

*Acqousto-Optic Products*, Brimrose Corporation, Baltimore, Maryland (Jan. 1992).

Pearson, L. H., "Diffuse Reflectance IR Spectroscopy for Bonding Surface Contamination Characterization," *Proceedings of the Review Progress in Quantitative Nondestructive Evaluation*, (Jul. 1990).

Carl, R. T., and Smith, M. J., "Material Analysis by Infrared Microimaging," *Review of Progress in Quantitative Nondestructive Evaluation*, vol. 9, (1990).

(List continued on next page.)

*Primary Examiner*—Constantine Hannaher
*Attorney, Agent, or Firm*—Ronald L. Lyons; Madson & Metcalf

[57] ABSTRACT

A scanning system (10) for inspecting a surface (16) including a light source (30) which generates a beam of light (32) that is reflected, scattered or causes fluorescence at the surface to be inspected. An optical interface (14) receives the beam of light and directs it along a predetermined path extending to and from the surface. An acousto-optic tunable filter (34) tuned to pass light having a wavelength corresponding to a known optical property of a predetermined material is positioned within the path of light. A detector (42) is positioned to receive light emanating from the surface and is configured to monitor the intensity of light at each predetermined wavelength being monitored and generate a corrsponding signal. The system is preferably attached to a scan board (90) thereby enabling the system to be used in scanning a surface. The system also includes a signal processor (22) which processes the signal generated by the detector. The resulting data is displayed by an output device (26).

26 Claims, 6 Drawing Sheets

U.S. PATENT DOCUMENTS

| | | | |
|---|---|---|---|
| 2,650,307 | 8/1953 | Koppius | 250/339.12 |
| 2,706,253 | 4/1955 | Hutchins et al. | 250/339.07 |
| 2,775,160 | 12/1956 | Foskett et al. | 356/418 |
| 2,897,371 | 7/1959 | Hasler | 378/50 |
| 3,017,512 | 1/1962 | Wolbert | 250/349 |
| 3,048,699 | 8/1962 | Francis | 250/338.1 |
| 3,153,722 | 10/1964 | Bayly et al. | 250/339.12 |
| 3,373,281 | 3/1968 | McAlister | 250/253 |
| 3,433,052 | 3/1969 | Maley | 374/5 |
| 3,451,254 | 6/1969 | Maley | 374/5 |
| 3,457,412 | 7/1969 | Cary | 250/351 |
| 3,471,698 | 10/1969 | Mausteller et al. | 250/351 |
| 3,603,952 | 9/1971 | Smith | 340/539 |
| 3,653,765 | 4/1972 | Hearn | 356/306 |
| 3,661,462 | 5/1972 | Nathens | 356/51 |
| 3,675,019 | 7/1972 | Hill et al. | 250/350 |
| 3,693,025 | 9/1972 | Brunton | 250/340 |
| 3,700,898 | 10/1972 | MacLeod | 250/343 |
| 3,734,621 | 5/1973 | Moody et al. | 356/325 |
| 3,747,755 | 7/1973 | Senturia et al. | 209/559 |
| 3,783,284 | 1/1974 | McCormack | 250/339.11 |
| 3,803,414 | 4/1974 | Van Horne et al. | 250/339.09 |
| 3,904,880 | 9/1975 | Benz et al. | 250/343 |
| 3,994,586 | 11/1976 | Sharkins et al. | 356/73 |
| 4,015,127 | 3/1977 | Sharkins | 250/341.3 |
| 4,085,326 | 4/1978 | Williams | 250/339.11 |
| 4,274,091 | 6/1981 | Decker | 340/583 |
| 4,320,967 | 3/1982 | Edgar | 356/51 |
| 4,345,150 | 8/1982 | Tamura et al. | 250/339.1 |
| 4,363,966 | 12/1982 | Cheo | 250/338.1 |
| 4,406,545 | 9/1983 | Montone et al. | 356/380 |
| 4,410,273 | 10/1983 | Mantz et al. | 356/319 |
| 4,427,889 | 1/1984 | Müller | 250/339.11 |
| 4,433,239 | 2/1984 | Thompson | 250/255 |
| 4,490,845 | 12/1984 | Stienbrugge et al. | 356/300 |
| 4,527,062 | 7/1985 | Novinson | 250/351 |
| 4,590,574 | 5/1986 | Edmonds et al. | 364/498 |
| 4,602,342 | 7/1986 | Gottlieb et al. | 364/498 |
| 4,616,134 | 10/1986 | Pruett et al. | 250/255 |
| 4,622,845 | 11/1986 | Ryan et al. | 73/24.02 |
| 4,652,756 | 3/1987 | Ryan et al. | 250/343 |
| 4,653,908 | 3/1987 | Yajima et al. | 356/51 |
| 4,663,961 | 5/1987 | Nelson et al. | 73/24.02 |
| 4,677,298 | 6/1987 | Zelmanovic et al. | 250/341.8 |
| 4,690,553 | 9/1987 | Fukamizu et al. | 356/51 |
| 4,718,026 | 1/1988 | Long et al. | 364/550 |
| 4,736,103 | 4/1988 | Nelson et al. | 250/343 |
| 4,771,629 | 9/1988 | Carlson et al. | 73/23.85 |
| 4,787,750 | 11/1988 | Nelson et al. | 356/437 |
| 4,808,824 | 2/1989 | Sinnar | 250/339.11 |
| 4,822,169 | 4/1989 | Distl et al. | 356/364 |
| 4,883,963 | 11/1989 | Kemeny et al. | 250/339.11 |
| 4,965,452 | 10/1990 | Sturm | 250/339.11 |
| 5,036,203 | 7/1991 | Solomon | 250/370.06 |
| 5,070,242 | 12/1991 | McClelland et al. | 250/339.03 |
| 5,120,961 | 6/1992 | Levin et al. | 250/339.07 |

OTHER PUBLICATIONS

*New Product Announcement: AOTF Spectrometer* [and Schematic], Infrared Fiber Systems, Inc., Silver Springs, Maryland (Oct. 1989).

Pearson, L. H., "IR Spectroscopy for Bonding Surface Contamination Characterization," *Proceedings of the Review of Progress in Quantitative Nondestructive Evaluation* (Aug. 1989).

*DCI 4000 Series Multi Axis Stepping Motor Controller Instruction Manual,* Design Components, Inc., Franklin, Massachusetts (Aug. 1988).

Ira Kurtz et al., "Rapid scanning fluorescence spectroscopy using an acousto–optic tunable filter," *Rev. Sci. Instrum.,* vol. 58, No. 11, pp. 1996–2003 (Nov. 1987).

[Untitled Instructions and Schematics for Positioning Table], Design Components, Inc., Franklin, Massachusetts (date unknown).

*Nicolet IR Microspectroscopy* [advertisement], Nicolet Corporation, Madison, Wisconsin (date unknown).

Hunt, J. H., "SurfS (Surface Spectroscopy)," Rockwell International, Rocketdyne Division (date unknown).

ACOUSTO-OPTIC TUNABLE FILTER-BASED SURFACE SCANNING SYSTEM AND PROCESS

CROSS-REFERENCE TO RELATED APPLICATIONS

This is a continuation-in-part of application Ser. No. 07/873,937, filed Apr. 24, 1992, now abandoned.

BACKGROUND

1. The Field of the Invention

The present invention is related to a system and process for inspecting surfaces. More particularly, the present invention is related to a system for obtaining near real time, nondestructive detection and evaluation of various materials on surfaces by directing light at the surface and analyzing the intensity and polarity of the light emanating from the surface at a wavelength corresponding to a known optical property of a predetermined material.

2. Technical Background

A typical manufacturing process utilized in many applications is the bonding of two materials. The criticality of the strength of the bond will vary depending on the particular application for which the bonded material is to be used. For example, in the manufacture of solid rocket motors, bond strength is particularly critical.

The bonds in a solid rocket motor can be subjected to forces of high magnitude due to acceleration, ignition pressurization and thermal loads. A weak bond or area of debonding can be the source of stress risers which can result in further weakening of the bond, eventually leading to failure of the bond, and can distort the geometry of the bonded material thereby adversely affecting the firing characteristics of the motor.

In the manufacture of a solid rocket motor, a variety of materials must be successfully bonded to one another. For example, some of the bonds found in a typical solid rocket motor are the bond between the case and the insulator, between the insulator and the liner, between the liner and the propellant and between the nozzle phenolic and the metal nozzle housing. A weak bond or debond in any of these bonds could result in catastrophic failure of the rocket motor.

When two materials are bonded together, contaminants on the surface of either of the materials can weaken the bond and, in some instances, cause areas of debonding. Organic materials such as greases, hydraulic fluids and mold release agents are the primary source of contamination of bonding surfaces in solid rocket motors. Other contaminants include particulates such as sand or dust. Oil vapors are often present in environments where hydraulic systems and electric motors are present. These vapors can condense on surfaces to be bonded. Even small levels of these contaminants, not visible to the human eye, can degrade bond strength.

The extent to which a surface can be cleaned prior to bonding and the method to be utilized in cleaning the surface vary according to the nature of the surface. For example, the rocket case of the space shuttle is a grit-blasted steel surface. It is typically cleaned by a vapor degrease process. According to one such process, the case is suspended within a pit in the bottom of which boiling methylchloroform is located. The methylchloroform evaporates and condenses on the rocket case. As it runs off the rocket case, it dissolves any grease in its path. While this process works well in cleaning small amounts of grease from the rocket case, if there are areas of localized buildup of grease, not all of the grease may be removed by the cleaning process.

Using a solvent such as methylchloroform to clean a bonding surface may not be viable if the bonding surface is a phenolic material. In a solid rocket motor the nozzle is typically made of a phenolic material. The nozzle is made by wrapping uncured tape onto a mandrel, permitting the tape to cure and then machining the part into the desired shape.

Phenolic materials will absorb virtually any type of cleaning solvent with which they come into contact. These solvents can alter the surface chemistry and/or carry dissolved contaminants into the phenolic. In applications such as those discussed herein, the surface properties of the phenolics must remain unchanged.

Presently, the preferred method of cleaning a phenolic material is to place it on the mill and machine a new surface, thereby removing the contaminated surface. However, this can only be done if the tolerances of the part permit a portion of the surface to be removed. Otherwise, a contaminated part may have to be replaced.

Because even small levels of contaminants, not visible to the human eye, can degrade bond strength, bonding surfaces must be inspected prior to bonding to ensure that there is no contamination, or that if there is contamination, it is within acceptable limits.

A crude method of conducting a surface inspection is to place some solvent on a wipe and stroke the surface with the wipe thereby transferring surface contaminants to the wipe. The wipe may then be analyzed using standard spectroscopy methods to verify the existence of contaminants on the wipe and determine their identity.

A principal obstacle to the successful use of this method is that it can only be used as a check method. It cannot be used as an inspection method on the entire bonding surface. And, while the method may provide information about the existence of a contaminant and its identity, it cannot be used to determine the thickness of the contamination. It is a qualitative method and therefore does not provide a quantitative measurement of the contamination. Additionally, this method cannot be used with phenolic materials because the surface chemistry of the phenolics would be altered by passing a wipe permeated with solvent over it.

A more versatile surface inspection method is to conduct a visual inspection with the aid of an ultraviolet light. Some contaminants, particularly grease such as that used for rust protection, fluoresce under ultraviolet light. Thus, by visually inspecting the surface under ultraviolet light, any contaminants which fluoresce under the light can readily be detected.

A disadvantage of this method is that the method cannot be reliably used to detect low levels of contamination as it is limited by what can be seen with the human eye. Additionally, this method, being manual in nature, does not provide machine-readable data. Consequently, the person performing the visual inspection must attempt to record the location and size of the contaminated area. As with many manual methods, the possibility of human error renders this method inadequate for many applications.

Automated inspection methods include an optically stimulated electron emission ("OSEE") method. This method is based on the photoelectric effect. By shining ultraviolet light on the surface to be inspected, electrons are emitted from the surface. By placing an electrode near the surface and raising the electrode to a predetermined voltage, an electric field is generated, drawing an electron current from the surface whose strength can be monitored. If there is contamination on the surface, the current is impeded. A disadvantage with the OSEE method is that it is subject to many variables which are not relevant to the determination of contamination. Such variables may include air currents surrounding the device being tested, relative humidity and moisture on the surface. Also, the OSEE method only works effectively on metals. It is ineffective as a tool to inspect phenolic or rubber surfaces.

Thus, it would be an advancement in the art to provide a system for the inspection of bonding surfaces which would detect the presence of thin films, including low-level contamination or surface coatings, which may not be detectible with prior-art visual inspection methods.

Indeed, it would also be an advancement in the art if such a surface inspection system could work effectively to detect contamination on a variety of surfaces and with different levels of roughness, including metal, phenolic and rubber surfaces.

It would be yet a further advancement in the art to provide such a system that could work efficiently and effectively in inspecting large surface areas.

Such a system for inspecting surfaces is disclosed and claimed herein.

BRIEF SUMMARY AND OBJECTS OF THE INVENTION

The present invention is directed to a novel system for inspecting surfaces to detect and characterize thin films, including contaminants. The system includes a light source capable of generating a beam of light and an optical interface for receiving the beam of light from the light source. The optical interface directs the beam of light along a predetermined path extending to and from the surface. An acousto-optic tunable filter is positioned within the path of light and is tuned to pass light having a wavelength corresponding to a known optical property of the material for which inspection is sought. Such optical properties may include traditional physical properties, such as absorption characteristics, as well as other, more general properties, such as spectral signatures which are indicative of a particular material.

A detector is positioned to receive light emanating from the surface. The detector is capable of monitoring the intensity of light at at least one predetermined wavelength and generates a signal corresponding to the intensity of each wavelength being monitored. The signal generated by the detector is fed into a signal processor which processes the signal and generates data concerning the characteristics of the surface.

The system also includes means for moving the system relative to the surface such that the surface may be scanned with the beam of light.

In one embodiment, the system may be used to detect and measure thin films, such as contamination or coatings, for which absorption properties are known. A presently preferred system includes a light source optimized for near to mid infrared wavelengths. The incident beam of light is passed through a spectrometer having an acousto-optic tunable filter. The spectrometer is preset to monitor the absorbance of at least the absorption band of one predetermined material and at least one reference band outside the absorption band.

An optical interface is provided to receive the incident beam of light from the spectrometer and focus it onto a discrete location on the surface to be inspected. The optical interface is also configured to gather a portion of the beam scattered off the surface and direct it into a detector. The detector generates a signal corresponding to the intensity of the detected light and transmits that signal to a computer for processing. The data processed by the computer is preferably translated into a graphical image by an output device, either in the form of a color (including a gray scale) image/display or a surface map of the contamination.

For rough metal surfaces, including machined or gritblasted metal surfaces, the optical interface is preferably adjusted to gather a portion of the back-scatter component of the scattered beam. For smooth surfaces or rough nonmetallic surfaces, it is presently preferred to adjust the optical interface to gather a portion of the specular component of the scattered beam. The angle of incidence for smooth surfaces and rough nonmetallic surfaces is chosen to be at or near the Brewster angle.

The incident beam is polarized when it is passed through the acousto-optic tunable filter. The filter separates the beam into two orthogonal components of linearly polarized light which exit the filter at different angles. In a preferred embodiment, the optical interface includes a partition positioned to block one of the components of polarized light from being directed onto the surface. It is currently preferred that the incident beam be vertically polarized, i.e., that component of the incident beam which is polarized parallel to the incident plane of light.

When utilizing a polarized incident beam, the gathered portion of the scattered beam is preferably passed through an analyzing polarizer. The orientation of the analyzing polarizer with respect to the incident polarized beam may be adjusted to maximize the ability to detect absorbance. When inspecting rough metal surfaces, it is preferred to orient the analyzing polarizer to pass the 90 degree depolarized portion of the beam.

In a preferred embodiment, a scanning apparatus is employed to rapidly change the point on the surface at which the beam of light is directed, thereby permitting the inspection of various locations on the surface or of large surface areas. By synchronizing the signal processing and the scanning of the surface, data concerning materials on the surface is generated. In one embodiment of the invention, successful scanning for contamination has been accomplished by directing the beam of light at discrete locations on the surface which are spaced about 0.10 inches (0.22 cm) apart and changing the point on the surface at which the beam of light is directed about every 0.01 seconds.

To obtain data concerning the thickness of a material on the surface as well as the existence of the material, an embodiment of the invention measuring absorbance of the incident beam of light is utilized in combination with calibration plates. Such calibration plates may include one plate with no contamination and one plate with a known amount of contamination. By scanning calibration plates prior to inspecting a surface, the linear relationship between absorbance and thickness of contamination may be determined. Because the thickness of the contamination is proportional to the absorption band size, once the linear relationship between absorbance and thickness is defined, the thickness of the contamination may readily be determined.

In another embodiment of the invention, the infrared light source is replaced with an ultraviolet light source capable of generating an incident beam of light including wavelengths in the ultraviolet range, i.e. generally from about 150 nm to about 400 nm.

The incident beam is preferably polarized with a polarizer before being directed onto the surface. Also, it is preferred to modulate the incident beam with a chopper wheel so that the effects of ambient light may be eliminated.

The polarized incident beam of ultraviolet light is directed onto the surface by the optical interface. Upon striking the surface, the ultraviolet light including light in the fluorescence inducing wavelength of the surface causes excitation of valence electrons inducing them to temporarily jump to a higher energy state. The fluorescence inducing wavelength is that wavelength of light which causes the material for which inspection is sought to fluoresce. Upon dropping to an intermediate energy state, photons in the visible spectrum corresponding to the fluorescent wavelength of the material are emitted from the surface. Because the wavelength of the emitted fluorescent light generated by this phenomenon is characteristic of the material producing it, the existence of a particular material on the surface can be ascertained by monitoring for light at a fluorescent wavelength of that material.

In this embodiment which utilizes an ultraviolet incident beam of light, the optical interface is also configured to gather at least a portion of the light emitted from the surface. The acousto-optic tunable filter is positioned to receive the gathered portion of the fluorescent beam and is tuned to pass light corresponding to the fluorescent wavelength of the material for which inspection is sought.

Because of the positioning of the acousto-optic tunable filter, it acts as an analyzing polarizer. Thus, the acousto-optic tunable filter polarizes the gathered fluorescent beam and separates it into two orthogonal components of linearly polarized light which exit the filter at two different angles. Detectors are positioned to receive each component of polarized light transmitted by the acousto-optic tunable filter and generate a signal corresponding to the intensity of the detected light.

In accordance with the teachings of the present invention, the light source, optical interface and acousto-optic tunable filter may be mounted on a scan board and included as part of the end effector of a robotic arm or other apparatus to accomplish scanning of the surface to be inspected. So configured, the system of the present invention may be utilized to provide near real-time data concerning the characteristics of a surface.

DETAILED DESCRIPTION OF THE PREFERRED EMBODIMENTS

Figure 1:
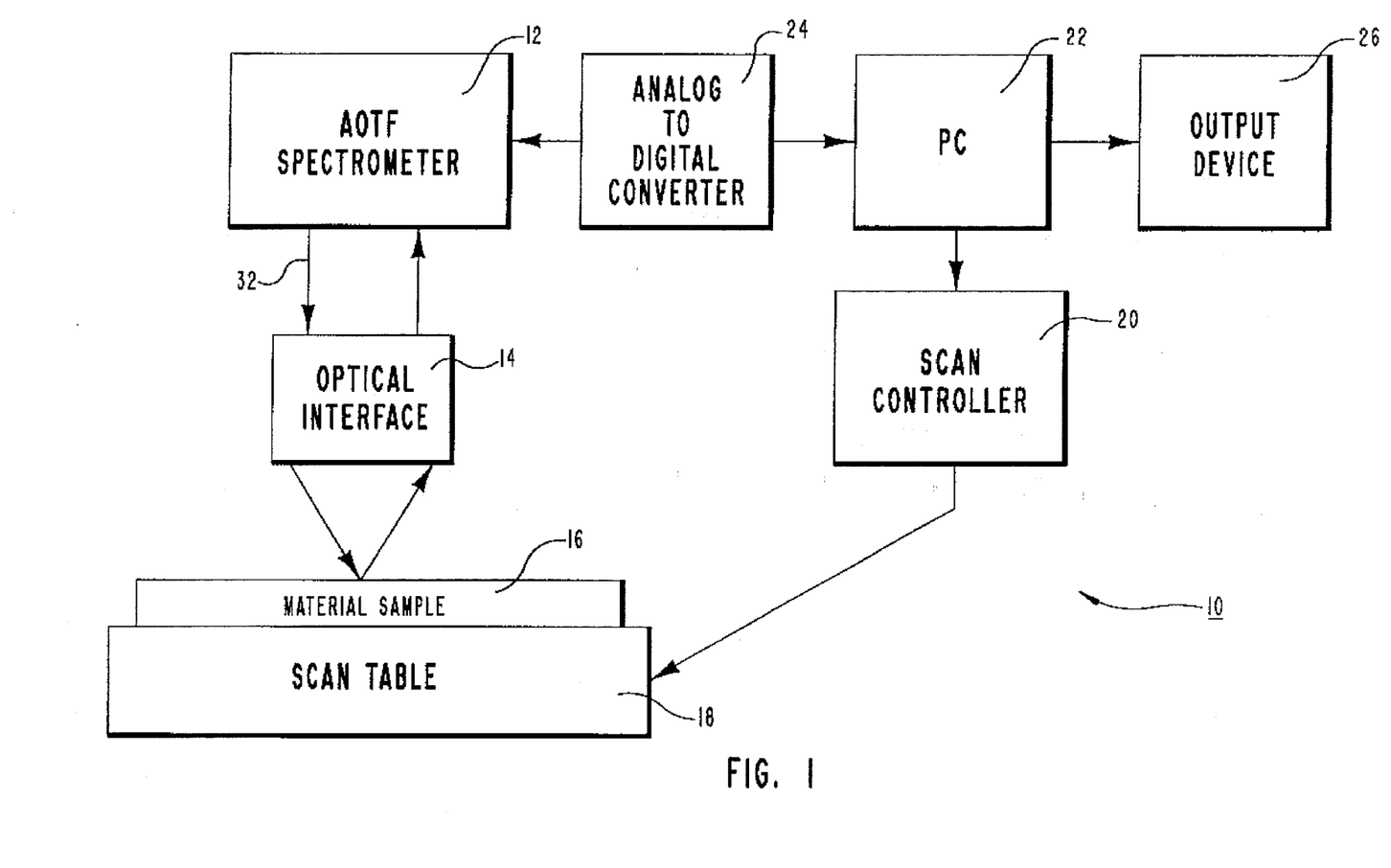
FIG. 1 is a schematic of the components comprising one embodiment of the surface scanning system of the present invention.

Reference is now made to the figures wherein like parts are referred to by like numerals throughout. With particular reference to FIG. 1, one embodiment of a system for inspecting a surface for contamination in accordance with the present invention is generally designated at 10. The system of the present invention may be used to inspect for a variety of materials for which certain optical properties are known or can be ascertained.

Indeed, because of the use of the acousto-optic tunable filter in the system of the present invention, near real-time analysis may be conducted for a variety of materials having an optical property characterized by a signature wavelength. By way of illustration, such optical properties may include absorption characteristics or fluorescence inducing characteristics. Other optical properties may also be utilized within the scope of the present invention.

The present invention is particularly useful when the material for which inspection is sought is known or suspected to be found on the surface. For example, in the production of solid rocket motors wherein data concerning contamination on bonding surfaces is needed, inspection may be conducted for specific contaminants such as silicone mold release agents. In a manufacturing facility, the existence of hydraulic systems or electric motors frequently leads to the presence of oil vapors in the ambient air which condense on bonding surfaces. By utilizing the present invention, whether these vapors have condensed on bonding surfaces can be ascertained. Indeed, the present invention has been used successfully to inspect for oil and grease, such as HD2 grease commonly used for rust protection.

In one embodiment, the system 10 of the present invention includes a spectrometer having an acousto-optic tunable filter 12, sometimes referred to herein as an "AOTF spectrometer." It has been found that an AOTF spectrometer is capable of providing an optimal combination of fast processing time and spectral resolution. In a presently preferred embodiment of the invention, spectrometer 12 is a solid state spectrometer based on the acousto-optic tunable filter, such as is marketed by Infrared Fiber Systems, Inc. of Silver Spring, Md.

In communication with the spectrometer 12 is an optical interface 14. As explained below in greater detail, the optical interface directs a beam of light from the spectrometer 12 to a surface 16 being inspected. It also collects a portion of the scattered beam and directs it into the spectrometer for analysis.

In one embodiment of the present invention, the surface or substrate 16 being inspected is supported by a scan table 18. The scan table is controlled by a scan controller 20. Scan table 18 and scan controller 20 may be any of those controllers and tables which are commercially available, such as the 4000 Series controller and the HM-1212 table, both of which are sold by Design Components, Inc. of Franklin, Mass.

In accordance with the embodiment of the present invention illustrated in FIG. 1, the spectrometer 12 and optical interface 14 are held in a stationary position while the surface 16 being scanned is moved by the scan table 18. While such an embodiment is presently preferred for a laboratory scale model of the invention wherein small surfaces are being scanned, it is not the preferred embodiment if the surface to be inspected is a large surface, such as the bonding surfaces in a large solid-rocket motor.

Thus, it will be appreciated by one of skill in the art that the spectrometer 12 and optical interface 14 may be utilized in combination with a robotics system to accomplish surface inspection of large surfaces. In such an embodiment, the surface to be scanned is held in a stationary position while the spectrometer and optical interface are moved relative to the surface to obtain data from various discrete locations on the surface.

A signal processor such as a computer 22 is provided to control the motion of the scan controller 20 and process the signal produced by the spectrometer 12. Use of computer 22 permits the synchronization of the motion of the scan controller 20 with the processing of data acquired from the spectrometer 12, thereby providing information concerning the location of any contamination detected on the surface 16 during scanning. Computer 22 may be any type of computer commonly known among those skilled in the art for use in this type of application. An IBM-AT compatible computer has been found to work satisfactorily.

An analog-to-digital converter 24 is provided between the AOTF spectrometer 12 and the computer 22 for converting the analog signal generated by the spectrometer into a digital signal which can be processed by the computer 22. It will be appreciated by one of skill in the art that analog-to-digital converter 24 may be integral with either the spectrometer 12 or the computer 22, as many AOTF spectrometers currently available on the market are equipped with such a converter. Alternatively, the converter 24 may be a separate component of the system 10.

An output device 26 is provided in communication with the computer 22 for providing a display of the data generated during the examination of surface 16. The output device 26 may include any device known among those skilled in the art for displaying data, including a video monitor or plotter. It may provide the data in either human-readable or machine-readable form. In one embodiment of the present invention, an EGA color graphics system has been found to provide satisfactory output.

The display of data may be accomplished in either graphical or numerical form. In a presently preferred embodiment of the invention, the data is displayed formatted in a manner to illustrate a surface map or a color scale image of the contamination. For graphical output, a color monitor may be used to display contour corresponding to various preassigned colors. Alternatively, a similarly formatted output may be illustrated in shades of gray.

Figure 2:
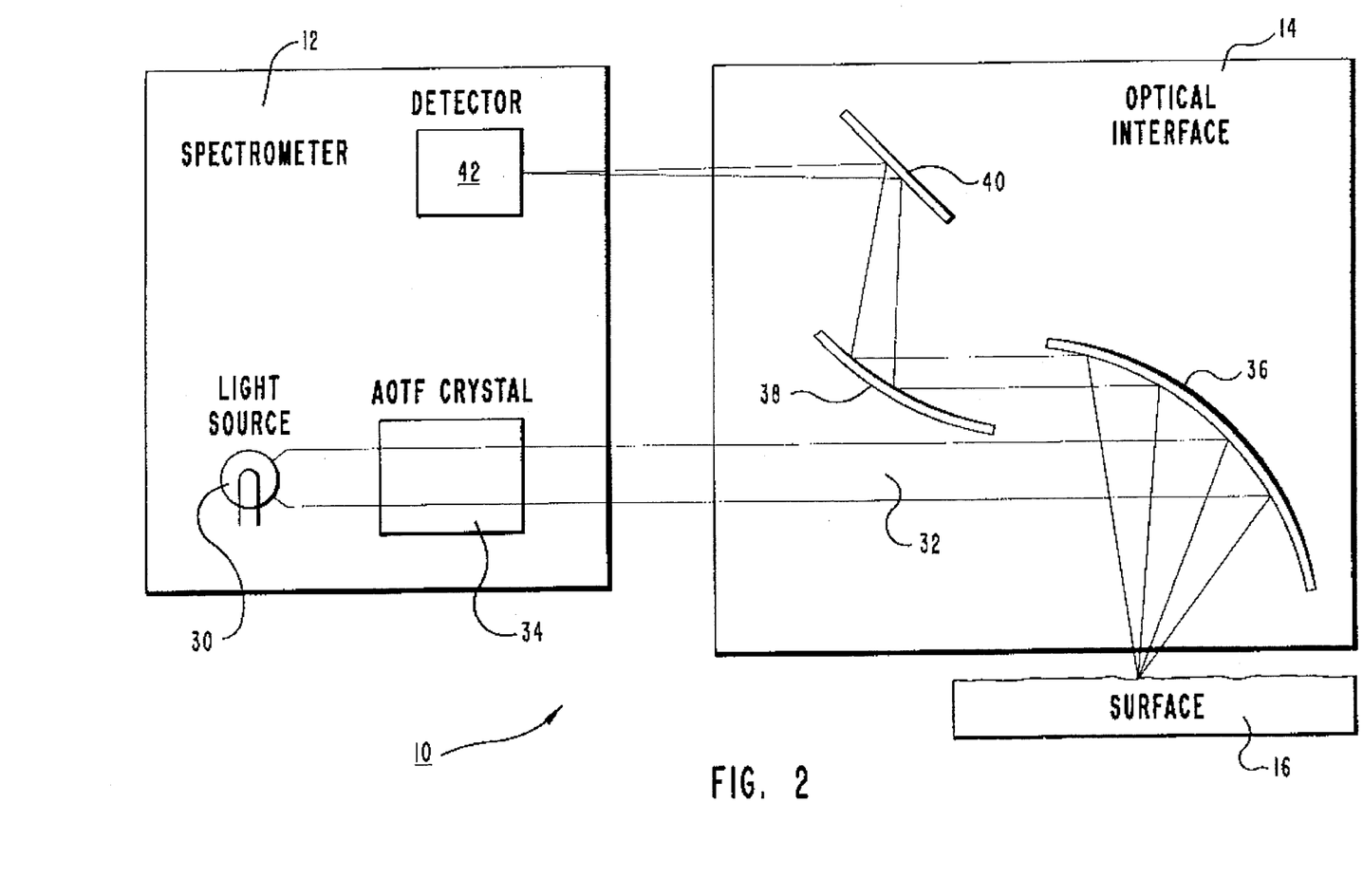
FIG. 2 is a schematic illustrating the components comprising the spectrometer and the optical interface of the system of FIG. 1 and illustrating a plan view of the path of the beam of light through the system.

As illustrated in FIG. 2, the AOTF spectrometer 12 includes a light source 30 which generates a beam of light 32. In this embodiment, light source 30 is preferably a quartz, halogen lamp such as that made by Gilway Technical Lamp of Woburn, Mass. Such a light source 30 is optimized for near to mid infrared wavelengths. In most commercially available AOTF spectrometers, light source 30 will be housed within the spectrometer. The spectrometer 12 is configured such that the beam of light 32 passes through the AOTF crystal 34 within the spectrometer. The crystal 34 acts to filter out all wavelengths of light from the beam 32 except those to be monitored by the system 10 during the surface inspection.

Before the beam 32 exits the AOTF spectrometer 12, the beam is transformed into a collimated beam. Upon its exit from the spectrometer 12, the collimated beam of light 32, including only those wavelengths of light to be monitored during the surface inspection, comes into contact with a first paraboloid mirror 36. First mirror 36 focuses the beam onto the discrete location on the surface 16 to be inspected. In this embodiment of the invention, first mirror 36 acts both to focus the incident beam on the surface and to gather a portion of the scattered component of the beam.

Figures 3, 4:
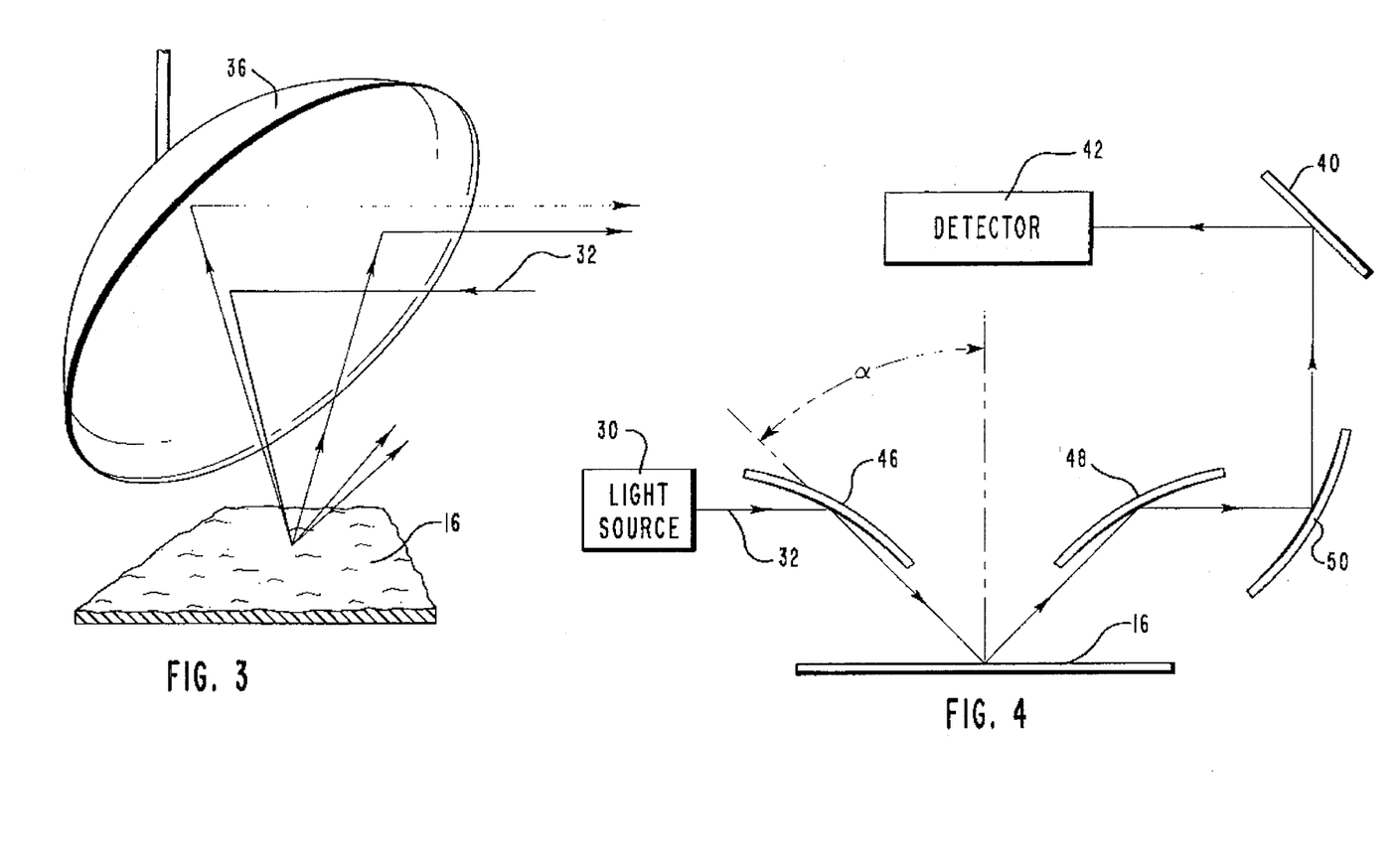
FIG. 3 is a perspective view of the paraboloid mirror and inspection surface of FIG. 1, illustrating how a portion of the back-scatter component of the scattered beam is gathered by the mirror.
FIG. 4 is a plan view of one embodiment of the present invention illustrating how a portion of the specular component of the scattered beam is gathered.

If the surface 16 to be inspected is a rough surface, such as is the case with most metal surfaces, first paraboloid mirror 36 is preferably positioned with respect to the surface such that it will gather a portion of the back-scatter component of the scattered beam, as is illustrated in FIGS. 2 and 3. As used herein, a surface is considered to be "rough" if its RMS (root mean square) roughness is on the order of a wavelength or greater than the wavelength of the light being employed by the method used to evaluate the surface.

If the surface being evaluated is one-dimensionally rough, as may be the case with a metal surface that has been machined, first paraboloid mirror 36 is preferably positioned with respect to the surface such that the incident beam is perpendicular to the parallel lines which comprise the roughness. One of the principal advantages of the present invention is that even if the surface is randomly rough, such as a grit-blasted metal surface, by positioning the paraboloid mirror 36 to collect a portion of the diffuse reflectance of the incident beam, meaningful data may be obtained from which contamination may be detected. Particularly where the surface roughness is fairly uniform, the effect of roughness may be removed from the data when the signal is processed.

Importantly, in accordance with the teachings of the present invention, surface roughness actually enhances the ability of the system of the present invention to detect and quantitatively measure surface contamination. Generally, the sensitivity of the present invention in detecting and measuring contamination is proportional to the intensity of the electric field created by the incident beam at the surface. Hence, as surface roughness increases, there is greater tendency for multiple scattering of light to occur at the surface which results in increased intensity in the electric field at the surface.

Because of this ability to successfully inspect rough surfaces, the present invention may be used to inspect surfaces of phenolic materials—materials which have proved particularly difficult to inspect by other methods. Carbon phenolics, for example, which have a surface which is generally treated as randomly rough even when machined, can be efficiently and effectively inspected by practicing the teachings of the present invention.

For a rough metallic surface, such as that illustrated in FIGS. 2 and 3, it is presently preferred to direct the beam at the surface at an incident angle in the range of from about 30 degrees to about 40 degrees.

The present invention may also be used on smooth surfaces, defined as surfaces having a RMS roughness less than the wavelength of light being used by the inspection method. For smooth surfaces, or rough surfaces of non-metallic materials, the first paraboloid mirror 36 is preferably positioned with respect to the surface 16 such that the mirror 36 will gather a portion of the specular component of the scattered beam, as illustrated in FIG. 4. The angle of incidence α of the beam is at or near the Brewster angle. It is at the Brewster angle that the electric field intensity near the surface is the strongest for the normal component of the electric field. For a typical polymer, the Brewster angle would be approximately 45 to 50 degrees at infrared wavelengths.

The gathered portion of the scattered beam, whether it be taken from the back-scatter component (mirror 36 of FIGS. 2 and 3) or the specular component of the beam (mirror 48 of FIG. 4), is converted back into a collimated beam and directed into a second paraboloid mirror (mirror 38 of FIG. 2 or mirror 50 of FIG. 4). The second paraboloid mirror focuses the beam onto the detector 42 via a directing mirror 40. The detector signal is digitized by the analog-to-digital converter 24 and received by the computer 22 for analysis.

The use of directing mirror 40 is optional. In a presently preferred embodiment of the invention in which a cryogenically cooled detector 42 is utilized, a directing mirror is employed because the beam must be directed horizontally into the detector to avoid spilling the liquid nitrogen used to cool the detector. It will be appreciated by one of skill in the art, however, that a variety of configurations may be employed in connection with the optical interface 14 to accomplish the purpose of the optical interface—directing and focusing the beam onto the surface and gathering a portion of the scattered component of the beam and directing it back into the spectrometer.

In operating this embodiment of the invention, the AOTF spectrometer 12 is initially set to monitor the absorbance band of a predetermined material. It is presently preferred that the band selected be that corresponding to the peak absorbance of the material sought to be located by the inspection. For example, if the material is a hydrocarbon, the absorption band is centered from between about three microns to about four microns, with 3.4 microns being preferable. In a presently preferred embodiment of the invention, the AOTF spectrometer 12 is set to inspect for a single material. However, if it is desired to simultaneously inspect for a variety of materials, the AOTF spectrometer could be set to monitor the peak absorbance of each. Simultaneously monitoring two or more materials may be even more practical as spectrometer technology improves to the point that AOTF spectrometers having a wider band capability become available on the market.

The AOTF spectrometer should also be set to monitor at least one reference band outside of the absorption band of any of the materials being monitored. It is presently preferred that two reference bands be monitored, one on each side of the absorption band of the material being monitored. Monitoring a reference band provides a basis for evaluating the absorption band of the material to determine whether variations in the measured absorbance of the absorption band are due to the presence of the material or due to external factors such as fluctuations or variations in surface roughness. For example, if the surface is being inspected for the presence of a hydrocarbon having an absorption band of 3.4 microns, preferred reference bands are 3.24 microns and 3.6 microns. If it is desired to inspect a surface for silicone release agents, an absorption band of about eight microns may be monitored. When inspecting for silicone release agents it is presently preferred to monitor an absorption band of 7.95 microns and monitor reference bands of 7.7 microns and 8.3 microns.

Once the AOTF spectrometer 12 has been preset, the system is preferably calibrated prior to use. Because the relationship between the thickness of the material on the surface and the amount of absorbance is approximately linear, the zero point and slope of that linear relationship must be determined by calibration in order to calculate the thickness of the material from the absorption data.

Calibration is performed by obtaining a calibration plate made of the same material and having the same roughness as the substrate to be inspected. In a preferred embodiment, five predetermined thicknesses of contamination are applied to approximately five different locations on the plate, thereby providing a sufficient number of data points that the relationship between absorption and thickness can readily be determined. The calibration plate should be representative of both the material type and the roughness level of the surface to be inspected.

The system 10 should be calibrated each time the substrate to be inspected is changed. Also, each time the mirrors are adjusted or the angle of incidence of the beam is altered, the system should be calibrated to regenerate the calibration curve.

With the system calibrated, it is ready to be used to inspect surface 16. In use, as illustrated in FIGS. 1 through 4, the beam of light 32 is focused onto a discrete location on the surface 16 by the optical interface 14. The optical interface 14 then gathers up a portion of the scattered beam and directs the beam into the detector 42 of the AOTF spectrometer 12. As discussed previously, if the surface being inspected is rough and metallic, it is preferred that a portion of the backscatter component of the scattered beam be analyzed; if the surface is smooth, or if it is rough and non-metallic, a portion of the specular component of the scattered beam is preferred.

The detector 42 of the AOTF spectrometer 12 analyzes the absorbance of the bands being monitored by generating a signal corresponding to the intensity of light at the absorption band. This analog signal is converted to a digital signal by the analog-to-digital converter 24. The digital signal is then processed by the computer 22. Having been previously calibrated, the computer compares the absorbance of the absorption band with that of the reference band and generates data indicating whether the material for which inspection is sought is present and provides information concerning its thickness and location on the surface.

Figure 5:
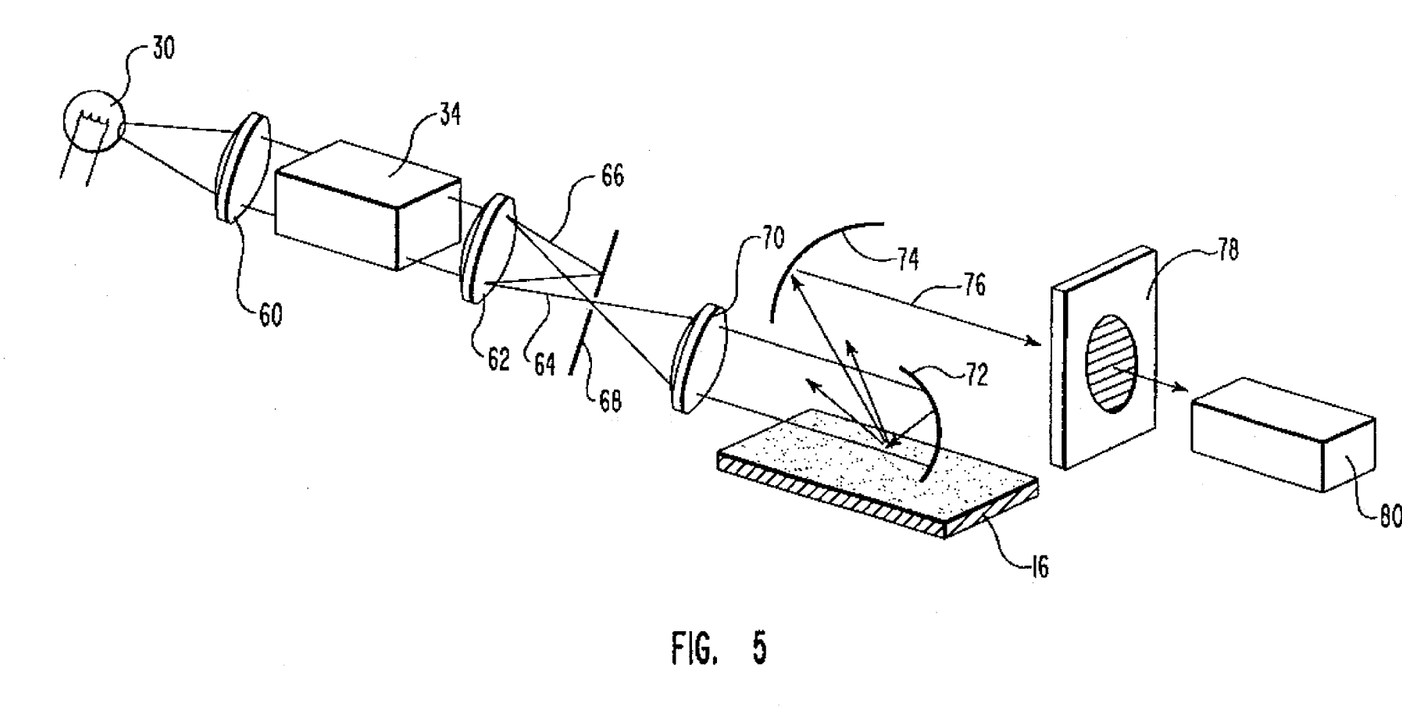
FIG. 5 is a schematic illustrating an alternative embodiment of the present invention.

An alternative embodiment of the present invention is illustrated in FIG. 5. As with the previously discussed embodiment, light source 30 is optimized for near to mid infrared wavelengths. In this embodiment, the optical interface includes a lens 60 configured to receive the beam of light from the light source 30 and direct it into the acousto-optic tunable filter 34. Another lens 62 receives the light exiting from the filter 34.

The acousto-optic tunable filter 34 is tuned to pass light corresponding to the absorption band of the material for which inspection is sought and at least one reference band outside the absorption band, as discussed above. The filter 34 is inherently configured to linearly polarize the incident beam to produce two orthogonal components of polarized light, a vertical component 64 and a horizontal component 66, exiting the filter 34 at different angles. The "vertical" component 64 is termed vertical because the polarization is vertically oriented with respect to the plane containing the incident beam, i.e., the plane normal to the paper in FIG. 5. In this embodiment, the two components of light exiting the filter are separated by an angle of about 12 degrees.

It has been found that the ability of the system to measure absorbance is enhanced if the vertical component 64 of the incident beam is utilized. Thus, a partition 68 is included in the optical interface, positioned to block the horizontal component 66 from being directed onto the surface 16.

The optical interface further includes a lens 70 through which the incident beam is collimated and directed to an incident mirror 72 where it is focused on the surface 16. A collecting mirror 74 is included in the optical interface for gathering a portion of the scattered beam 76. As described above, the roughness of the surface will generally dictate how the collecting mirror 74 is positioned to gather a particular portion of the scattered light.

The polarization of the incident beam is modified upon interaction with the surface 16. Thus, by passing the gathered portion of the scattered beam 76 through a polarizing analyzer, the amount the incident beam has been depolarized by the surface can be analyzed. Thus, an analyzing polarizer 78 is positioned to receive the gathered portion of the scattered beam 76. Analyzing polarizer 78 may include virtually any polarizers, such as those which are commercially available.

A detector 80 is positioned to receive the gathered portion of the scattered beam 76 as it exits the analyzing polarizer 78. As with the detector in the previously discussed embodiment, detector 80 generates a signal corresponding to the intensity of light it detects. As will be appreciated by one of skill in the art, the processing of the data and the hardware necessary for such processing is substantially the same as that outlined in connection with the previously described embodiment.

Figure 6:
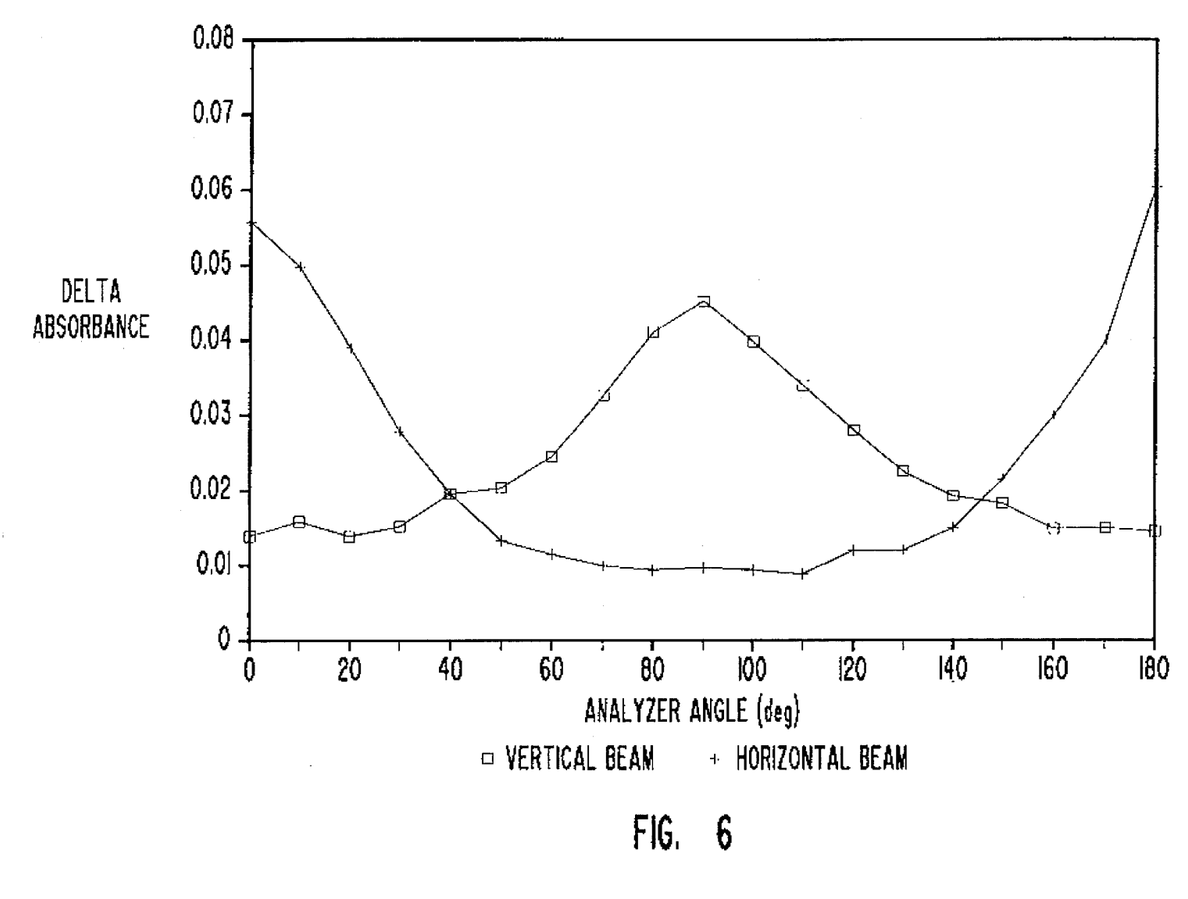
FIG. 6 is a graph charting the amount of absorbance measured on a rough metal surface as a function of angle of orientation of the analyzing polarizer.

It has been found in some applications that by varying the angular orientation of the analyzing polarizer 78, the ability of the system to measure absorbance data varies. In particular, when scanning rough metal surfaces, by orienting the analyzing polarizer 78 to pass the 90 degree depolarized portion of the beam, the ability of the system to detect absorbance appears to be maximized. The graph of FIG. 6 charts the amount of absorbance measured on a rough metal surface as a function of angle of orientation of the analyzing polarizer. As illustrated in FIG. 6, absorbance is maximized at an analyzing polarizer angle of approximately 90 degrees.

Accordingly, when utilizing this embodiment of the present invention to inspect rough metal surfaces, the analyzing polarizer 78 is preferably positioned to pass the 90 degree depolarized portion of the beam 76. This is generally achieved by rotating the analyzing polarizer 90 degrees with respect to the incident polarization (in this embodiment, provided by the acousto-optic tunable filter 34). This is illustrated in FIG. 5 with the analyzing polarizer 78 positioned to pass the horizontal component of the gathered portion of the scattered beam.

Figure 7:
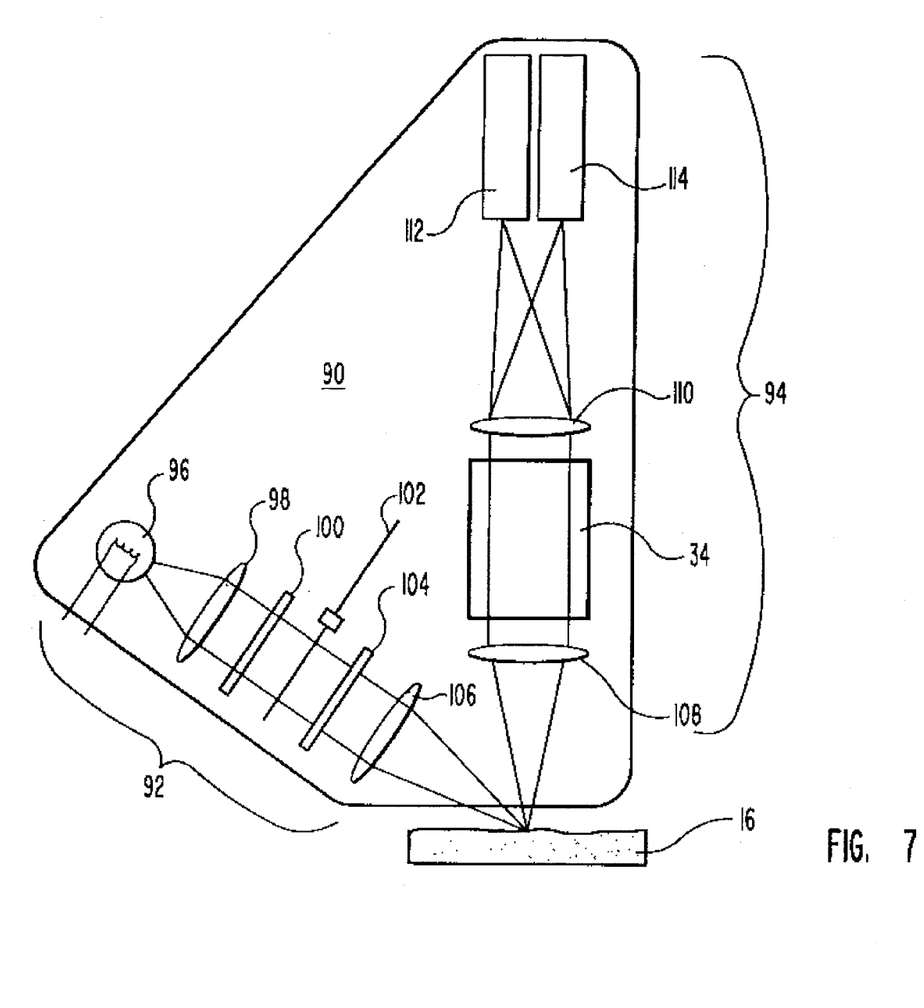
FIG. 7 is a schematic illustrating an additional alternative embodiment of the present invention.

An additional alternative embodiment of the present invention is illustrated in FIG. 7. This embodiment of the present invention is illustrated with the light source, optical interface and acousto-optic tunable filter mounted on a scan board 90. When attached to such a scan board, the present invention may easily be included as part of the end effector of a robotic arm or other apparatus to accomplish scanning of the surface to be inspected.

When positioned on a scan board, a source optics train 92 and a receiving optics train 94 are generally defined. The source optics train 92 generates the incident beam, prepares it for application to the surface and directs it to the surface. The receiving optics train 94 is configured to gather a portion of the light emanating from the surface, process the gathered light and generate a signal corresponding to detected intensity.

The scan board preferably encloses the source and receiving optics trains 92 and 94. An enclosed scan board would, of course, be configured with an opening through which light may be directed onto the surface to be inspected and through which light emanating from the surface may be gathered for analysis. Enclosing the optics trains would facilitate cooling of the hardware, reduce the exposure of the optics to dust and reduce the amount of ambient light which enters into the system.

One of skill in the art will appreciate that the utilization of optics trains to configure various embodiments of the present invention on a scan board or other hardware to facilitate use of the invention in scanning may be readily accomplished. Indeed, for particular applications it may be desirable to configure an apparatus including a plurality of source and receiving optic trains designed to simultaneously inspect for various materials. Alternatively, such a configuration may be desirable merely to provide a single apparatus having the capacity of inspecting for one of a variety of materials, as the application might require.

In the embodiment of FIG. 7, the light source 96 generates an incident beam of light including wavelengths in the ultraviolet range, i.e. generally from about 150 nm to about 400 nm. Such a light source may include any of those commercially available ultraviolet lights, such as a mercury vapor lamp.

The optical interface includes a lens 98 which focuses the light into a parallel beam and directs it into an optical filter arrangement 100. In this embodiment, the optical filter arrangement preferably comprises a band-pass filter configured to pass light at the fluorescence inducing wavelength of the material for which inspection is sought, as is explained in greater detail below.

A chopper wheel 102 is positioned in the source optics train 92 and is configured with a series of blades which intercept the incident beam as it is emitted from the light source 96. The chopper wheel is configured to rotate at a predetermined rate such that the light emitted from the light source 96 is modulated.

The effects of any ambient light entering the system are substantially eliminated by modulating the incident beam with the chopper wheel 102. Any ambient light which does penetrate the system is not detected by any of the detectors as having a modulated amplitude. Because the system is designed to detect only the modulated component of the detected signal, the presence of ambient light does not affect the measurement of the system.

The source optics train 92 also preferably includes a polarizer 104 for polarizing the incident beam. Another lens 106 focuses the incident beam onto the surface 16.

The receiving optics train 94 includes a lens 108 which gathers a portion of the light emanating from the surface 16 and directs the gathered portion of light into the acousto-optic tunable filter 34. The acousto-optic tunable filter 34 is tuned to pass light corresponding to the fluorescent wavelength of the material for which inspection is sought.

Positioned in the receiving optics train 94, the filter 34 acts as an analyzing polarizer, producing two orthogonal components of polarized light. A lens 110 directs these two components of light into detectors 112 and 114 which generate a signal corresponding to the intensity of the detected light. Processing of that signal proceeds utilizing substantially the same hardware and following the same processes as outlined in connection with other embodiments of the invention.

In operation, the light source 96 is selected to include the fluorescence inducing wavelength of the material for which inspection is sought. The optical filter arrangement 100 is also selected to pass light having the fluorescence inducing wavelength of the material for which inspection is sought.

As the surface 16 is scanned, presence of the material for which inspection is sought will result in the emission of a fluorescent beam having a fluorescent wavelength characteristic of that material. Hence, the acousto-optic tunable filter 34 is tuned to pass light at the fluorescent wavelength of the material for which inspection is sought.

Advantageously, the utilization by the present invention of the optical property of fluorescence to inspect for a material on a surface provides the invention with an expanded group of materials for which inspection may be conducted. This embodiment may be effectively utilized in identifying the presence and location of organic materials such as grease, many oils and silicone based materials. Additionally, inorganic materials, such as zirconium silicate particulates and cloth or dust particulates, may also be identified with this embodiment.

This embodiment of the present invention is easily calibrated by inspecting a surface known not to fluoresce at the fluorescent wavelength to be utilized in the system. Such a reading provides a baseline, or zero signal level, against which fluorescence from the surface to be inspected may be measured.

While the present invention may be used to inspect a single portion of a surface, it is preferably used to inspect an entire surface by inspecting discrete locations on the surface. For large surfaces, such as the bonding surfaces of solid rocket motors, a robotics system may be utilized. Alternatively, the system may be used in combination with scan table 18 to inspect smaller surfaces which are capable of being placed on the scan table.

Use of the AOTF spectrometer 12 permits the analysis of a variety of discrete locations of a surface to be conducted quickly, thereby enabling the system of the present invention to be efficiently used in analyzing large surface areas. Once data has been obtained from one location of the surface, the system may be utilized to inspect an adjacent location of the surface and the process repeated until representative samples of the entire surface have been inspected. With data from representative samples of the entire surface, the computer 22 can generate an output on output device 26 indicating both the location of any contamination as well as its thickness.

It is presently contemplated that the surface scanning system 10 be configured to permit surface scanning rates on the order of inches (centimeters) per second. However, one skilled in the art will appreciate that the surface scanning rate may be adjusted according to the requirements of the particular application. For example, tolerance for contaminants for some applications may be less stringent than for others, thereby permitting measurements to be taken farther apart and permitting faster scanning.

In one embodiment of the present invention, for each pixel on a graphic image representing 0.10 inches (0.22 cm) of a surface scan, a system built and operated in accordance with the teachings of the present invention is capable of averaging tens to hundreds of surface measurements. So configured, the system provides a good signal-to-noise ratio and generates sufficiently reliable data for most purposes.

As previously discussed, this data may be output in either graphical, numerical or machine-readable form. In graphical form, the data may be displayed as an image in which a different color or shade of gray is designated as corresponding to a predetermined thickness of the contamination. In a presently preferred embodiment of the invention, such a color scale image is preferred.

Alternatively, a surface image could be generated which appears as a three dimensional image on the screen. A surface image is advantageous for graphically illustrating relative thickness of the contamination as compared to background noise level. A disadvantage to surface images is that some of the information is hidden by the peaks generated.

The computer 22 is ideally programmed to synchronize the processing of the signal received from the detector with the movement of the beam of light with respect to the surface being inspected. The synchronization of these two functions enables the computer to generate output correlating the measured data with the precise location on the surface to which it corresponds. One of ordinary skill in the art will appreciate that there are a variety of ways to program a computer to accomplish this stated objective.

From the foregoing it will be appreciated that the present invention provides a system for the inspecting of surfaces to detect the presence of materials on a surface, including low levels of materials which are generally not accurately detectible by visual inspection methods. The present invention may be utilized to detect contamination on a variety of surfaces, including rough and smooth surfaces and surfaces made of metal, rubber and phenolics. Importantly, the present invention provides an efficient and effective system for inspecting large surface areas for contamination.

It should be appreciated that the apparatus and methods of the present invention are capable of being incorporated in the form of a variety of embodiments, only a few of which have been illustrated and described above. The invention may be embodied in other forms without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by patent is:

1. A system for scanning a rough surface to obtain near real-time data concerning characteristics of the surface, comprising:

a light source capable of generating a beam of light;

an optical interface configured to receive the beam of light from the light source and direct the beam of light along a predetermined path extending to and from the surface, the optical interface including means for directing the beam onto a discrete location on the surface;

an acousto-optic tunable filter positioned within the path of light, the filter tuned to pass light having a wavelength corresponding to a known absorption band of a predetermined material and at least one reference band outside the absorption band;

a polarizer positioned within the path of light for polarizing the beam of light before it is directed onto the surface;

an analyzing polarizer positioned within the path of light for analyzing the polarization of light scattering off the surface;

a detector positioned to receive light passing through the analyzing polarizer, the detector capable of monitoring the intensity of light at the absorption band of the predetermined material and at the reference band, the detector capable of generating a signal corresponding to the intensity of each wavelength being monitored;

a signal processor in communication with the detector for processing the signal generated by the detector; and means for moving the directing means relative to the surface such that the surface may be scanned with the beam of light.

2. A system for scanning a surface as defined in claim 1, wherein the analyzing polarizer is oriented to pass the 90 degree depolarized portion of the beam when the surface being scanned is a metallic surface.

3. A system for scanning a surface as defined in claim 1, wherein the means for moving the directing means relative to the surface comprises a scan board to which the light source, the optical interface, the acousto-optic tunable filter and the detector are attached.

4. A system for scanning a rough surface to obtain near real-time data concerning characteristics of the surface, comprising:

a light source capable of generating an incident beam of light;

an optical interface configured to receive the incident beam of light from the light source and direct the incident beam onto a discrete location on the surface, the optical interface further configured to gather at least a portion of the beam which is scattered off the surface;

an acousto-optic tunable filter positioned to receive the incident beam, the filter tuned to pass light corresponding to the absorption band of a predetermined material and at least one reference band outside the absorption band, the acousto-optic tunable filter being inherently configured to linearly polarize the incident beam to produce two orthogonal components of polarized light exiting the filter at different angles, the optical interface further including a partition positioned to block one of the components of polarized light from being directed onto the surface;

an analyzing polarizer positioned to receive the gathered portion of the scattered beam;

a detector positioned to receive the gathered portion of the scattered beam from the analyzing polarizer, the detector capable of monitoring the intensity of light at the absorption band of the predetermined material and at the reference band, the detector capable of generating a signal corresponding to the intensity of each wavelength being monitored;

a signal processor in communication with the detector for processing the signal generated by the detector; and means for moving the optical interface relative to the surface such that the surface may be scanned with the beam of light.

5. A system for scanning a surface as defined in claim 4, wherein the optical interface is further configured to gather at least a portion of the back-scatter component of the scattered beam when the beam is scattered off a metallic surface.

6. A system for scanning a surface as defined in claim 4, wherein the optical interface is further configured to gather a portion of the specular component of the scattered beam when the beam is scattered off a non-metallic surface.

7. A system for scanning a surface as defined in claim 4, wherein the light source emits light in the near to mid infrared range.

8. A system for scanning a surface as defined in claim 4, wherein the acousto-optic tunable filter and the optical interface are positioned relative to the surface such that the component of the incident beam directed onto the surface is vertically polarized.

9. A system for scanning a surface as defined in claim 4, wherein the analyzing polarizer is oriented to pass the 90 degree depolarized portion of the beam when the surface being scanned is a metallic surface.

10. A system for scanning a surface as defined in claim 4, wherein the means for moving the optical interface relative to the surface comprises a scan board to which the light source, the optical interface, the acousto-optic tunable filter and the detector are attached.

11. A system for scanning a surface to obtain near real-time data concerning characteristics of the surface, comprising:

a light source capable of generating an incident beam of light including wavelengths in the ultraviolet range;

an optical interface configured to receive the incident beam of light from the light source and direct the incident beam onto a discrete location on the surface, the optical interface further configured to gather at least a portion of the fluorescent beam emitted from the surface;

a polarizer positioned to polarize the incident beam of light;

an acousto-optic tunable filter positioned to receive the gathered portion of the fluorescent beam, the filter tuned to pass light corresponding to the fluorescent wavelength of a predetermined material;

a detector positioned to receive the fluorescent beam emitted from the surface, the detector capable of monitoring the intensity of light at the fluorescent wavelength of the predetermined material, the detector capable of generating a signal corresponding to the intensity of the wavelength being monitored;

a signal processor in communication with the detector for processing the signal generated by the detector; and means for moving the optical interface relative to the surface such that the surface may be scanned with the beam of light.

12. A system for scanning a surface as defined in claim 11, further comprising a modulator for modulating the incident beam such that the effect of any ambient light at the fluorescent wavelength of the predetermined material is substantially eliminated.

13. A system for scanning a surface as defined in claim 11, further comprising an optical filter arrangement positioned to filter the incident beam of light and configured to pass light having wavelengths corresponding to the fluorescence inducing wavelength of the predetermined material.

14. A system for scanning a surface as defined in claim 13, wherein the optical filter arrangement includes a band-pass filter.

15. A system for scanning a surface as defined in claim 11, wherein the acousto-optic tunable filter is inherently configured to linearly polarize the gathered portion of the fluorescent beam to produce two orthogonal components of polarized light exiting the filter at different angles and wherein the detector includes a first detector positioned to receive one component of the polarized light exiting the filter and a second detector positioned to receive the other component of polarized light exiting the filter.

16. A process for scanning a rough surface to obtain near real-time data concerning characteristics of the surface, comprising the steps of:

generating an incident beam of light with a light source;

passing the incident beam of light through an acousto-optic tunable filter tuned to pass light corresponding to the absorption band of a predetermined material and at least one reference band outside the absorption band;

polarizing the incident beam;

directing the incident beam of light passed through the acousto-optic tunable filter onto a discrete location on the surface;

gathering at least a portion of the beam scattered off the surface;

directing the gathered portion of the scattered beam through an analyzing polarizer;

introducing the gathered portion of the scattered beam into a detector capable of monitoring the intensity of light at the absorption band of the predetermined material and at the reference band, the detector capable of generating a signal corresponding to the intensity of each wavelength being monitored;

analyzing the intensity of the gathered portion of the scattered beam at the absorption band of the predetermined material and at the reference band; and selecting a different discrete location on the surface and repeating the preceding steps.

17. A process for scanning a surface as defined in claim 16, wherein the step of gathering at least a portion of the beam scattered off the surface includes gathering at least a portion of the back-scatter component of the scattered beam when the beam is scattered off a metallic surface.

18. A process for scanning a surface as defined in claim 16, wherein the step of gathering at least a portion of the beam scattered off the surface includes gathering at least a portion of the specular component of the scattered beam when the beam is scattered off a non-metallic surface.

19. A process for scanning a surface as defined in claim 16, wherein the step of polarizing the incident beam comprises polarizing the incident beam with the acousto-optic tunable filter to produce two orthogonal components of polarized light exiting the filter at different angles and blocking one of the components of polarized light from being directed onto the surface.

20. A process for scanning a surface as defined in claim 16, wherein the step of polarizing the incident beam includes producing a vertically polarized beam and the step of directing the incident beam onto a discrete location on the surface includes directing the vertically polarized beam onto a discrete location on the surface.

21. A process for scanning a surface as defined in claim 20, wherein the step of directing the gathered portion of the scattered beam through an analyzing polarizer comprises directing the gathered portion of the scattered beam through an analyzing polarizer oriented to pass the 90 degree depolarized portion of the beam when the surface being scanned is a metallic surface.

22. A process for scanning a surface to obtain near real-time data concerning characteristics of the surface, comprising the steps of:

generating an incident beam of light including wavelengths in the ultraviolet range;

passing the incident beam through a polarizer to polarize the incident beam of light;

directing the incident beam onto a discrete location on the surface;

gathering at least a portion of the fluorescent beam emitted from the surface;

passing the gathered portion of the fluorescent beam through an analyzing polarizer;

passing the gathered portion of the fluorescent beam through an acousto-optic tunable filter tuned to pass light corresponding to the fluorescent wavelength of a predetermined material;

introducing the light passed through the acousto-optic tunable filter into a detector capable of monitoring the intensity of light at the fluorescent wavelength of the predetermined material, the detector capable of generating a signal corresponding to the intensity of the wavelength being monitored;

analyzing the intensity of the gathered light at the fluorescent wavelength of the predetermined material; and selecting a different discrete location on the surface and repeating the preceding steps.

23. A process for scanning a surface as defined in claim 22, further comprising the step of substantially eliminating the effect of ambient light at the fluorescent wavelength of the predetermined material by modulating the incident beam with a chopper wheel.

24. A process for scanning a surface as defined in claim 22, wherein the step of directing the incident beam onto a discrete location on the surface includes passing the incident beam of light through an optical filter arrangement configured to pass light having wavelengths corresponding to the fluorescence inducing wavelength of the predetermined material.

25. A process for scanning a surface as defined in claim 22, wherein the step of passing the gathered portion of the fluorescent beam through an analyzing polarizer includes passing the gathered portion of the fluorescent beam through the acousto-optic tunable filter to produce two orthogonal components of polarized light exiting the filter at different angles.

26. A process for scanning a surface as defined in claim 25, wherein the step of introducing the light passed through the acousto-optic tunable filter into a detector includes introducing one of the orthogonal components of the polarized light exiting the filter into a first detector and introducing the remaining orthogonal component of the polarized light exiting the filter into a second detector.

* * * * *